United States Patent [19]

Anbar et al.

[11] 4,427,884

[45] Jan. 24, 1984

[54] METHOD FOR DETECTING AND QUANTIFYING CARBON ISOTOPES

[75] Inventors: Michael Anbar, Buffalo; Robert C. Abbott, Williamsville, both of N.Y.

[73] Assignee: The Research Foundation of State University of New York, Albany, N.Y.

[21] Appl. No.: 342,147

[22] Filed: Jan. 25, 1982

[51] Int. Cl.$^3$ .................. B01D 59/44; H01J 49/26
[52] U.S. Cl. .................. 250/283; 250/288; 436/173
[58] Field of Search .............. 250/283, 282, 281, 288, 250/424; 436/173; 313/362; 315/111.8

[56] References Cited

U.S. PATENT DOCUMENTS 3,786,249 1/1974 Anbar et al. ............... 250/288 X
3,885,155 5/1975 Anbar ........................ 250/283
4,224,031 9/1980 Mee et al. .................... 436/173

*Primary Examiner*—Alfred E. Smith
*Assistant Examiner*—Jack I. Berman
*Attorney, Agent, or Firm*—Michael L. Dunn; Howard M. Ellis

[57] ABSTRACT

A method for detecting and quantifying a carbon isotope at quantities of less than $1 \times 10^{-12}$ gram at a statistical precision of better than 5% in a time period of less than 5 minutes by producing a carbon compound, selected from $CO, CS_2, CO_2$ and elemental carbon, from the carbon containing composition to be analyzed; and producing and detecting sufficient $C^-$ ions from the carbon compound at a known efficiency to provide at least 80 counts of carbon isotope ions per minute by mass spectrometry.

14 Claims, No Drawings

METHOD FOR DETECTING AND QUANTIFYING CARBON ISOTOPES

BACKGROUND OF THE INVENTION (A) Field of the Invention

This invention relates to analytical methods for detecting and quantifying carbon isotopes and more particularly relates to the quantification of carbon isotopes by mass spectrometry.

(B) History of the Prior Art

The most common method for detecting and quantifying carbon 14 is scintillation counting of the radioactive decomposition of the carbon 14 isotope. The non-radioactive and more common $^{12}C$ and $^{13}C$ isotopes cannot be determined by this method since they are non-radioactive.

Amounts of carbon 14 of less than $1 \times 10^{-11}$ gram cannot be quantitatively determined by scintillation counting in less than five minutes with a statistical precision of 5% or better and quantities of less than $1 \times 10^{-12}$ (one trillionth) gram of carbon 14 cannot be quantitatively determined by scintillation counting in less than one hour with a statistical precision of 5% or better. When a statistical precision of 1% or better is required, it would take over two hours to quantitatively determine less than $1 \times 10^{-11}$ gram of carbon 14 and over a day to quantitatively determine less than $1 \times 10^{-12}$ gram of carbon 14. Determination of quantities below $1 \times 10^{-12}$ gram of carbon 14 becomes completely impractical by this method over any period of time due to the interference of background radiation.

The detection and quantification of carbon 14 in an amount even as low as $1 \times 10^{-12}$ gram are quantities which are undesirably high to permit the use of carbon 14 as an in vivo biological radioactive tracer in humans. In order to obtain a sample from the person upon which a tracer study is being made, which contains an analyzable quantity of carbon 14, the person must be exposed to a much larger quantity of carbon 14. All of the carbon 14 injected into the person would almost certainly not become concentrated in the sample taken from the person and, in addition, since the sample being considered must be adjusted for the biological half life of the compound, a substantial excess of carbon 14 would initially be required to compensate for loss due to biological excretion or biochemical transformation.

These considerations could therefore easily require an exposure to carbon 14 of 100,000 to 1,000,000 times the carbon 14 contained in the sample obtained for analysis. The quantity required to be injected becomes even greater when shorter times for analysis (e.g., less than 5 minutes) are required due to short residence time in automated analytical equipment. Furthermore, when better analytical precision is desired (e.g., a statistical precision better than 5%), even higher quantities of carbon 14 must be injected.

In addition, scintillation counting is an unsatisfactory method of dating materials by carbon 14 decay due to interference of background radiation and due to the inability of this method to determine carbon 14 to carbon 12 ratios at small sample size within a reasonable period of time, even if the effects of background radiation could be sufficiently reduced, e.g., by conducting the method in a salt mine.

Prior art carbon dating was originally accomplished by gas phase counting, (a method less sensitive than scintillation counting) and was then subsequently accomplished by scintillation counting which is a method which is not as sensitive as desired as previously discussed.

Carbon 14 dating has been accurately accomplished by the use of particle accelerators to obtain highly positively charged carbon atoms which were then separated by mass spectrometry and then directly or indirectly counted. This method requires extremely costly equipment and requires relatively large sample sizes.

An attempt has been made to determine carbon 14 by converting carbon to $CO_2$, mixing the $CO_2$ with nitrogen, converting the mixture to $CN^-$ ions and determining the quantity of $^{14}C^{15}N^-$ by mass spectrometry (U.S. Pat. No. 3,885,155). Unfortunately, this method is insufficiently sensitive for use in carbon 14 biological tracer studies and in carbon 14 dating tests due to interference of ionic species of essentially the same charge to mass ratio as $^{14}C^{15}N^-$. Particularly troublesome interfereing ions are $^{29}Si^-$ and $^{28}Si_iH^-$. The silicon is difficult, if not impossible, to sufficiently exclude since it forms a part of the material of the construction of the instrument, i.e., as an impurity in the metallic materials or as a component in glass.

BRIEF DESCRIPTION OF THE INVENTION

There is therefore provided, in accordance with the present invention, a method for detecting and quantifying a carbon isotope (including all carbon isotopes) at quantities of less than $1 \times 10^{-12}$ gram at a statistical precision of better than 5% within a time period of less than about 5 minutes. The method comprises producing a carbon compound selected from the group consisting of elemental carbon, CO, $CS_2$ and $CO_2$ from the carbon containing composition to be analyzed and producing and detecting sufficient $C^-$ ions from the carbon compound at a known efficiency to provide at least 80 counts of carbon isotope ions per minute by mass spectrometry. The invention also includes a method for measuring the ratio of one isotope to another in a carbon containing composition with a statistical precision of better than 5% in less than 5 minutes. The method for measuring the ratio comprises producing the carbon compound from the carbon in the carbon containing composition. The carbon compound is selected from the group consisting of elemental carbon, carbon monoxide (CO), carbon dioxide ($CO_2$) or carbon disulfide ($CS_2$). Sufficient $C^-$ ions are produced and detected from the carbon compound to provide a sufficient number of counts of each carbon isotope by mass spectrometry to determine the ratio of the isotopes within the 5% statistical precision desired.

In accordance with the present invention, a novel method for providing the $C^-$ ions is employed wherein $C^-$ ions are produced by discharge ionization through the elemental carbon, carbon monoxide, carbon dioxide or carbon disulfide carbon compound in an excess of helium in the presence of cesium atoms.

DETAILED DESCRIPTION OF THE INVENTION

Essentially any carbon isotope can be detected and quantified in accordance with the method of the invention. The carbon isotopes which are usually detected and quantified, in accordance with the present invention, are carbon 12 ($^{12}C$), carbon 13 ($^{13}C$) and carbon 14 ($^{14}C$). Quantities of less than $1 \times 10^{-12}$ gram of a particular isotope can be easily detected and quantified in accordance with the method of the invention as can any quantity of a carbon isotope, e.g., $1 \times 10^{-13}$ gram, down to a quantity of about $1 \times 10^{-15}$ gram. In addition, such quantities can be quantified at a statistical precision of better than 5% and usually better than 1% within a time period of less than about 5 minutes and even substantially less than 1 minute.

Furthermore, the method of the invention can be used for measuring the ratio of one carbon isotope to another in a carbon containing composition with a statistical precision of better than 5% and usually easily better than 1% at ratios of one isotope to another of 1:1,000,000 or better. Furthermore, such ratios can be determined in less than 1 minute at a statistical precision of 1% or better.

The analytical method, in accordance with the present invention, does not depend upon radioactive decomposition but utilizes the known deviation of an ion of a given mass within a known magnetic or electrical field to direct the ion to an ion detector (mass spectrometry). The method of the invention permits detecting and quantifying a carbon isotope at quantities which are several orders of magnitude smaller than the quantities detectable by scintillation counting during the same period of time at the same statistical precision.

In accordance with the present invention, a carbon compound selected from the group consisting of elemental carbon, carbon monoxide (CO), carbon disulfide ($CS_2$) and carbon dioxide ($CO_2$) is produced from the carbon containing composition to be analyzed. Sufficient $C^-$ ions are then produced and detected from the carbon compound at a known producing and detecting efficiency to provide a sufficient number of counts per minute by mass spectrometry of ions of the carbon isotope to be detected and quantified.

The detecting efficiency is a known characteristic of the detector employed and the producing efficiency is usually determined by simultaneously producing ions from a known quantity of an isotope other than the isotope to be quantified. The ion producing efficiency can then be calculated for the known quantity of the isotope other than the isotope to be quantified. Since it can be assumed that the ion producing efficiency is the same regardless of the carbon isotope under consideration, the producing efficiency for the ions of the isotope to be detected and quantified is therefore determined. Since the producing efficiency can vary with time due to possible changes in the ion producing conditions, and even in the ion detecting conditions, an unknown quantity of an isotope is usually calculated as a ratio to a simultaneously detected quantity of a different known carbon isotope.

The ratio of one carbon isotope to another can be determined even if the producing and detecting efficiency is not known since the same producing and detecting efficiency will apply to both isotopes. In measuring the ratio of one carbon isotope to another in a carbon containing composition, a carbon compound is produced from the carbon in the carbon containing composition. The carbon compound is selected from the group consisting of elemental carbon, carbon monoxide, carbon dioxide and carbon disulfide. Sufficient $C^-$ ions of both isotopes are then produced and detected from the carbon compound to provide a sufficient number of counts of each carbon isotope by mass spectrometry to determine the ratio of the isotopes which is the same as the ratio of the number of counts. When the quantity of one of the isotopes is known prior to analysis by the method in accordance with the present invention, the quantity of the other isotope can, of course, be readily calculated from the quantity of known isotope.

In accordance with the present invention, $C^-$ ions are preferably produced by electrical discharge in a partial vacuum through a carbon compound, which is usually $CO_2$ in excess inert gas, which is usually helium, in the presence of alkali metal atoms, usually cesium. In accordance with the present invention, a carbon isotope can be analyzed at a statistical precision of better than 5% within a time period of less than about 5 minutes at a known efficiency when at least 80 counts per minute of ions of the carbon isotope to be detected and quantified are detected by the mass spectrometer. 2,000 counts per minute of ions of the carbon isotope to be detected and quantified are required when a statistical precision of better than 1% is desired within a time period of less than about 5 minutes and 10,000 counts of ions of the carbon isotope to be detected and quantified are required when a statistical precision of better than 1% is desired in less than 1 minute.

The method of the present invention is particularly desirable when the carbon containing composition to be analyzed is a minute quantity of carbon containing composition which has been separated by the chromatographic methods and which is then carried to a reaction chamber for conversion to elemental carbon, carbon monoxide, carbon disulfide or carbon dioxide followed by transporting the converted composition to an electrical discharge chamber for production of $C^-$ ions. The method of the invention is particularly suitable in such cases since the method can be utilized for detecting and quantifying a carbon isotope in a matter of seconds. The method therefore lends itself to permitting the use of carbon 14 as a biochemical tracer element and possibly to carbon 14 dating of very small quantities of carbon sample.

The following examples serve to illustrate and not limit the present invention.

EXAMPLE 1

To determine efficiency of $C^-$ ion production and detection in accordance with the invention, $CO_2$ of natural abundance was introduced into an electrical discharge chamber in the presence of cesium and then to a mass spectrometer at a concentration of 2.5 parts per million (volume to volume) in helium at a flow rate of 0.5 ml/min (STP) or $2 \times 10^{-5}/60 = 3.3 \times 10^{-7}$ moles per second. Under these conditions a $C^-$ current of 0.12 microamps ($7.4 \times 10^{12} C^-$ ions/sec) was measured at a mass to charge ratio (m/z) of 12. These results show a $C^-$ production and detection efficiency from $CO_2$ of about $1.8 \times 10^{-4}$ ions per $CO_2$ molecule. Under these conditions $3.3 \times 10^{-15}$ moles of $CO_2$ ($1.6 \times 10^{-14}$ grams of C) can be determined with a 1% precision ($10^4$ ions) when measuring the ion current for just $10^{-8}$ seconds and $3.3 \times 10^{-16}$ moles ($1.6 \times 10^{-15}$ grams C) can be determined with a 1% precision in just $10^{-7}$ seconds.

EXAMPLE 2

An ampoule containing 1 microcurie $^{14}C$ carrier free bicarbonate was diluted with triple distilled water down to a concentration of $2 \times 10^{-10}$ curie per ml. 0.1 ml of this solution ($2 \times 10^{-11}$ curie = $9.5 \times 10^{-11}$ g $^{14}C$) and was dried under vacuum in a 250 ml bulb containing 10 mg $NH_4Cl$. After the sample was completely dry, He containing 2.5 ppm $CO_2$ was introduced at atmospheric pressure and the NH$_4$Cl was heated to sublimation so that it reacted with the sodium bicarbonate in the presence of CO$_2$. Under these conditions, all the CO$_2$ underwent isotopic exchange and the bulb contained CO$_2$ labelled with $^{14}C$ at a specific activity of $2\times10^{-14}/2.5\times10^{-8} = 8\times10^{-4}$ curie/mole. Each ml in the bulb contained $2\times10^{-11}/250 = 8\times10^{-14}$ curie ($3.8\times10^{-13}$ g) $^{14}C$. The gas feed rate was approximately 1.0 ml STP/min or $2.5\times10^{-6}/2.5\times10^{-4} = 1\times10^{-10}$ moles CO$_2$/min, i.e., $6\times10^{13}$ molecules of CO$_2$. At the same time the feed rate of $^{14}CO_2$ was $8\times10^{-14}/64 = 1.3\times10^{-15}$ moles ($3.8\times10^{-13}$ g) or $1.3\times6\times10^{-15}\times10^{23} = 7.8\times10^{8}$ molecules $^{14}CO_2$. The expected ratio of $^{14}C/^{12}C$ was therefore $7.8\times10^{8}/6\times10^{13} = 1.3\times10^{-5}$. The mass to charge ratio (m/z) 14 ion count was actually $1.6\pm0.2\times10^{3}$ counts/sec. with a background of 42 counts/sec. At the same time the ion count at m/z 12, measured at a lower voltage on the electron multiplier and correcting for the difference in detection efficiency, was $8\pm2\times10^{7}$ counts/sec. The experimental $^{14}C/^{12}C$ ratio $= 2\times10^{-5}$ was therefore somewhat higher than expected. The sensitivity of detection was however over $10^{-4}$ C$^-$ ions/CO$_2$ molecule. The higher observed ratio is believed to be primarily due to inadequate cross calibration of the electron multiplier at its two voltages of operation. Also the sequential rather than simultaneous measurement of m/e 14 and 12 contributes to the lower precision of the ratio. This imprecision would be eliminated in a multiple collector instrument.

EXAMPLE 3

0.1 μc of $^{14}C$ alanine $10^{-2}$Ci/mole is injected IV to a septic patient. 10 minutes after injection, a blood sample of 1 ml is withdrawn. The sample is passed over a cation exchanger to remove the amino acids. The eluted amino acids are esterified with methanol in the presence of HCl and the mixture is separated on a GC with a gas carrier to give a peak of methylalaninate. The eluent from the GC is passed over CuO to oxidize the carbon to CO$_2$ and then over Molecular Sieves Sieves 3A to remove the water. The m/z=14 of the total peak is about 8500 counts. Assuming a detection efficiency of $1.3\times10^{-4}$, the number of $^{14}C$ labelled alanine molecules in the one ml of plasma are $3\times8500/1.3\times10^{-4} = 2\times10^{8}$, i.e., $2\times10^{8}/6\times10^{23} = 3\times10^{-16}$ moles or $3\times64\times10^{-16} = 2\times10^{-14}$ curie. Since the alanine pool is approximately 20000 ml, the expected level of alanine would be $5\times10^{-12}$ curies per ml if no metabolism was taking place. The result suggests that in our patient, the biological half life of alanine is of the order of 2 minutes, which fits the metabolic pattern of septic patients.

What is claimed is:

1. A method for detecting and quantifying a carbon isotope at quantities of less than $1\times10^{-12}$ gram at a statistical precision of better than 5% within a time period of less than about five minutes, said method comprising producing a carbon compound selected from the group consisting of elemental carbon, CO, CS$_2$ and CO$_2$ from the carbon containing composition to be analyzed and producing and detecting sufficient C$^-$ ions from the carbon compound at a known efficiency to provide at least 80 counts per minute by mass spectrometry of ions of the carbon isotope to be detected and quantified.

2. The method of claim 1 wherein carbon 15 is the isotope which is detected and quantified at quantities of carbon 14 of less than $1\times10^{-13}$ gram.

3. The method of claim 1 wherein the statistical precision is better than 1% and sufficient C$^-$ ions are produced to provide at least 2,000 counts of carbon isotope ions per minute.

4. The method of claim 2 wherein the statistical precision is better than 1% and sufficient C$^-$ ions are produced to provide at least 2000 counts of carbon 14 ions per minute.

5. The method of claim 1 wherein the isotope is carbon 14, the time period is less than one minute, the statistical precision is better than 1% and sufficient C$^-$ ions are produced to provide at least 10,000 counts of carbon 14 ions per minute.

6. The method of claim 2 wherein the time period is less than one minute and the statistical precision is better than 1% and sufficient C$^-$ ions are produced to provide at least 10,000 counts of carbon 14 ions per minute.

7. The method of claim 1 wherein the carbon isotope is detected and quantified at quantities of less than $1\times10^{-14}$ gram.

8. The method of claim 6 wherein carbon 14 is detected and quantified at quantities of less than $1\times10^{-14}$ gram.

9. The method of claim 1 wherein the producing and detecting efficiency is determined by detecting carbon 12 ions produced from a known quantity of $^{12}CO_2$.

10. The method of claim 1 wherein the carbon compound is CO$_2$ and the C$^-$ ions are produced by electrical discharge in a partial vacuum through the CO$_2$ in helium in the presence of cesium atoms.

11. A method for measuring the ratio of one carbon isotope to another in a carbon containing composition with a statistical precision of better than 5%, said method comprising producing a carbon compound from the carbon in the carbon containing composition, said carbon compound being selected from the group consisting of elemental carbon, carbon monoxide, carbon dioxide and carbon disulfide and producing and detecting sufficient C$^-$ ions from the carbon compound to provide a sufficient number of counts of each carbon isotope by mass spectrometry to determine the ratio of the isotopes within a 5% statistical precision.

12. The method of claim 11 wherein counts of the isotopes by mass spectrometry are detected and measured simultaneously.

13. A method for producing C$^-$ ions by electrical discharge in a partial vacuum through a carbon compound in an inert gas in the presence of cesium atoms, said compound being selected from the group consisting of elemental carbon, carbon monoxide, carbon dioxide and carbon disulfide.

14. The method of claim 13 wherein the inert gas is helium and the carbon compound is carbon dioxide.

* * * * *